United States Patent [19]
Serpelloni et al.

[11] Patent Number: 5,160,680
[45] Date of Patent: * Nov. 3, 1992

[54] METHOD FOR THE PREPARATION OF DIRECTLY COMPRESSIBLE GRANULAR MANITOL

[75] Inventors: Michel Serpelloni, Bethune; Patrick Lemay, Lestrem, both of France

[73] Assignee: Roquette Freres, Lestrem, France

[*] Notice: The portion of the term of this patent subsequent to May 16, 2006 has been disclaimed.

[21] Appl. No.: 605,157

[22] Filed: Oct. 31, 1990

Related U.S. Application Data

[63] Continuation of Ser. No. 262,195, Oct. 19, 1988, abandoned, which is a continuation of Ser. No. 783,528, Oct. 3, 1985, abandoned.

[30] Foreign Application Priority Data

Oct. 3, 1984 [FR] France .................. 84 15212

[51] Int. Cl.$^5$ ............. B29C 47/00; C07C 31/18
[52] U.S. Cl. ................... 264/126; 264/140; 264/211.11; 568/852; 568/868
[58] Field of Search ............ 264/40.7, 109, 123, 264/126, 140, 141, 211.11, 211.21, 176 R; 568/852, 868

[56] References Cited

U.S. PATENT DOCUMENTS

| | | | |
|---|---|---|---|
| 2,951,263 | 9/1960 | Cooper | 264/140 |
| 3,341,415 | 9/1967 | Scott | 264/13 |
| 3,966,857 | 6/1976 | Charlton et al. | 264/75 |
| 4,133,857 | 1/1979 | Takano et al. | 264/109 X |
| 4,302,413 | 11/1981 | Howe et al. | 264/126 |
| 4,831,129 | 5/1989 | Serpelloni | 536/124 |

FOREIGN PATENT DOCUMENTS

| | | |
|---|---|---|
| 54868 | 6/1982 | European Pat. Off. . |
| 2054599 | 2/1981 | United Kingdom . |

OTHER PUBLICATIONS

The Condensed Chemical Dictionary, 10th Edition, p. 644.

*Primary Examiner*—Leo B. Tentoni
*Attorney, Agent, or Firm*—Larson and Taylor

[57] ABSTRACT

The invention relates to a method of preparing directly compressible granular mannitol, wherein a raw material essentially constituted of powder mannitol is subjected to an extrusion treatment inside an installation comprising a heating zone and an extrusion die, the supply flow rate of the installation with raw material as well as the parameters of the extrusion treatment, namely the temperature existing inside the heating zone, the diameter of the extrusion die and the driving speed of the raw material inside the heating zone being selected so that at the exit of the die and before the exit of the mannitol from the latter, the mannitol is partly fused.

2 Claims, 2 Drawing Sheets

METHOD FOR THE PREPARATION OF DIRECTLY COMPRESSIBLE GRANULAR MANITOL

This application is a continuation of application Ser. No. 07/262,195 filed Oct. 19, 1988 which is a continuation of application Ser. No. 06/783,528 filed Oct. 3, 1985 both now abandoned.

The invention relates to a method for the preparation of directly compressible granular mannitol.

Mannitol, through its properties, particularly through its taste and its low hygroscopicity, constitutes a pharmaceutical excipient of quality when it is rendered directly compressible; but it does not show this property naturally particularly when it is obtained by crystallisation from water.

BACKGROUND OF THE INVENTION

Description of the Prior Art

Summary of the Invention

In the trade, there is already to be found directly compressible mannitol in granular form, with or without granulation binder.

When there is no binder, the compressibility of the product is not very satisfactory and the friability is moreover too high.

In addition, the presence of a binder—which counters the friability and increases compressibility—is not appraised very much by the user.

Consequently there existed a need for directly compressible granular mannitol not including binder and with compressibility and friability properties improved with respect to those of already-existing products.

It is this need that the Applicant's has attempted to satisfy.

And they had the merit of finding that it was possible to prepare such a directly compressible granular mannitol, freed from binder and of improved friability and compressibility properties, by subjecting powdered mannitol to an extrusion treatment of which the parameters of temperature, duration and pressure are selected so that at the outlet of the extrusion zone the so-treated mannitol is in the partly fused state.

In consequence, the method of manufacturing directly compressible granular mannitol according to the invention is characterized by the fact that a raw material essentially constituted from mannitol powder is subjected to an extrusion treatment inside an installation comprising a heating zone and an extrusion die or drawplate, the feed supply rate of the installation with raw material as well as the parameters of the extrusion treatment, namely the temperature existing inside the heating zone, the diameter of the extrusion die and the speed of driving the raw material inside the heating zone being selected so that at the outlet of the die and before the emergence of the mannitol from the latter, said mannitol is partly fused.

In an advantageous embodiment of the above-said method, the raw material is treated inside an extrusion installation of the dual-screw type comprising an extrusion die and the parameters of the extrusion treatment are selected so that the raw material is at a temperature of 160° to 170° C. and preferably, from 165° to 168° C. inside the die and before the emergence of the mannitol from the latter.

Under these conditions, it is estimated that the proportion of fused mannitol is from 30 to 90%, and more generally from 50 to 80%.

The time of passage of the mannitol through the extrusion installation is advantageously situated within a range of 0.5 to 10 minutes, preferably from 1 to 4 minutes.

The invention concerns also other features which are preferably used at the same time and which will be more explicitly considered below and it will, in any case, be well understood by means of the additional description which follows as well as the accompanying drawing and the example, said additional description and example relating to advantageous embodiments.

BRIEF DESCRIPTION OF THE PREFERRED EMBODIMENTS

In order, consequently, to manufacture, according to the invention, directly compressible granular mannitol without the intervention of a binder and having lower friability with respect to that of the directly compressible mannitol of the prior art, procedure is as follows or in equivalent manner.

The raw material which is subjected to the extrusion treatment is constituted from powdered mannitol essentially in the form of crystalline mannitol.

In practice, native mannitol crystals are used, that is to say crystals obtained conventionally by crystallization in water; in practice also, there is added to these native crystals, by recycling, the part of the mannitol obtained at the end of the method, which is not commercially utilizable, for example by reason of too low a granulometry.

The mannitol crystals in powder form are introduced into an extrusion installation, as the case may required, in the presence of a small amount of water at less than 4% and, preferably, less than 2%.

The temperature of these crystals is generally comprised, at the entry of the extrusion installation between 15° to 80° C. without this constituting a limiting factor of the invention.

Figure 1:
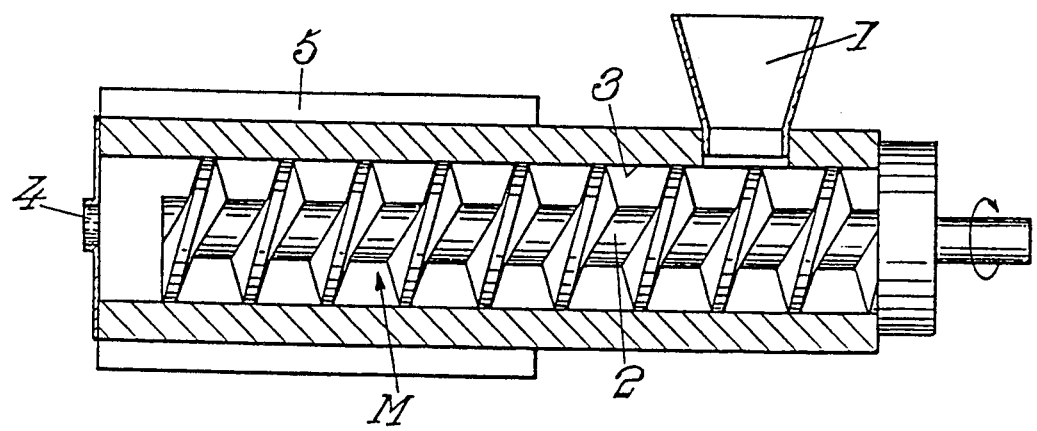
FIG. 1 of the drawing represents, in diagramatic section, an extrusion installation of the type which can be used within the scope of the method according to the invention.

The extrusion installation is constituted advantageously by an installation, or extruder, of the dual-screw type comprising, as shown in FIG. 1:

a supply system, particularly a measuring and mixing hopper, a malaxating zone M comprising an endless double screw system 2 positioned inside a casing 3, particularly of nitrided steel, and rotated by a mechanism not shown, an outlet comprising one or several dies 4 of different shapes, heating means 5 enabling the temperature of the malaxating zone to be controlled, these heating means 5 being constituted, for example, by electrical resistances, by an induction heating system or by steam and by cooling means (not shown) positioned outside the casing or inside it and shaped, for example, in the form of coils housed in the casing, a cooling fluid system housed inside the screw, and the like.

The raw material entering through the supply member into the malaxating zone is subjected, due to the compression produced in the turns of the screw, to intense shearing and mechanical friction simultaneously with the heating induced by the heating element.

The extrusion constitutes, consequently, a thermomechanical treatment.

To fix ideas, it is indicated that good results have been obtained with an extruder of the dual-screw type marketed under the name "BC 82" by the CREUSOT-LOIRE Company. The two screws penetrate into each other and rotate in the same direction. The malaxating zone is heated by induction and the temperature can hence easily be regulated.

The essential advantage of this heating mode is its flexibility in use and its easy control by means of a simple regulation loop (thermocouple/control device of the electrical supply of the induction heating means). It could be that the existence of an intense electromagnetic field exerts an influence on the properties of the product.

In the case of the installation used within the scope of the example described below, the die used was of cylindrical shape and had a diameter of 3 mm.

The temperature of the heating zone is obtained by imposing on the heating system a predetermined value. In the case of the extrusion installation which has just been considered, this value is comprised between 230° and 300° C., preferably between 260° to 300° C. and, more preferably still, in the neighborhood of 280° C.

The mechanical characteristics of the screws and their rotary speed are selected so that the time of the dwell of the raw material inside the heating zone is in the neighborhood of 2 minutes.

By means of the choice of all of these parameters the temperature of the raw material which has undergone treatment, is 165° to 168° C. inside the die and before its exit from the latter.

The mannitol obtained at the outlet of the extrusion installation is successively subjected:
to cooling,
to grinding,
to sifting and
to recycling of the fines (particles of too small a size to be retained by the smallest sieve of the installation) at the level of the supply of the extruder.

Before testing the performances in compression of mannitol thus obtained, a lubricant is incorporated, in the event, for example, magnesium stearate.

Below is given an example illustrating the method.

EXAMPLE

Crystalline mannitol of chemical purity above 98% and with a water content of 0.07%, is used to supply a "BC 82" extruder of the CREUSOT-LOIRE Company of the above-described type.

The speed of the screws is adjusted so that the flow rate of the installation is 250 kg/hour and the contact time 2 minutes.

The reference temperature of the heating system is programmed at 270° C., which permits a temperature of 166° C. to be obtained for the mannitol at the outlet of the extruder.

This mannitol is in the form of small rods which are ground by means of a grinder of the hammer type.

By sifting, the fines are separated which are recycled to the supply level of the extruder.

To show the advantage that there is in using, in the manufacture of directly compressible mannitol, the method according to the invention, comparative measurements and tests were made which will be described.

These tests bear:
on the directly compressible granular mannitol according to the example and, by way of comparison,
on a first directly compressible granular mannitol of the trade without binder, as well as
on a second directly compressible granular mannitol including 1.5% by weight of a binder constituted by gelatin.

First of all the granulometric distribution and the granulometry (corresponding to 50% of the average distribution by weight) of the different mannitol powders subjected to the comparative tests and particularly to the compression test, were determined.

The flow index of these powders was also determined by resorting to the method of CARR as described by CARR R. L. in Chem. Eng. 72, N°1, 163, 168 (1965) and Chem. Eng. 72, N°2, 69–73 (1965); to do this, an apparatus was used, known under the brand "HOSOKAWA POWDER TESTER" and manufactured by MICROMERITICS, Osaka (Japan).

The friability of these powders was also determined. This property is characterized as being represented by the percentage of particles which has not withstood crushing in an apparatus called a friabilimeter. In the event, one of the brand "ERWEKA TA" was used. This apparatus contained 5 identical steel balls of 1.7 cm diameter and 18.87 g each.

15 g of a granulometric fraction from 400 to 500 microns of the powder tested was introduced therein and the apparatus was spun at 25 rpm for 15 minutes.

By weighing, at the end of the crushing, the proportion was determined, expressed in %, represented by the residue retained by a sieve of mesh width 351 microns; the value of the friability corresponded to the complement to 100 of the latter value. The greater the figure thus obtained, the greater the friability; it is recalled that powders of low friability are sought.

Finally, the compressibility of these different powders was determined; this compressibility is manifested in terms of "breaking strength", expressed in Newtons and measured on tablets prepared by means of various mannitol powders.

The tablets were manufactured under a pressure of 196.133 MPa in a high-yield rotary press of the type P 1000 manufactured by the WILHELM FETTE GmbH Company (2503 Schwarzenbeck—Federal Republic of Germany or F.R.G.) and equipped with measuring gauges for the compressive and ejection forces.

Figure 2:
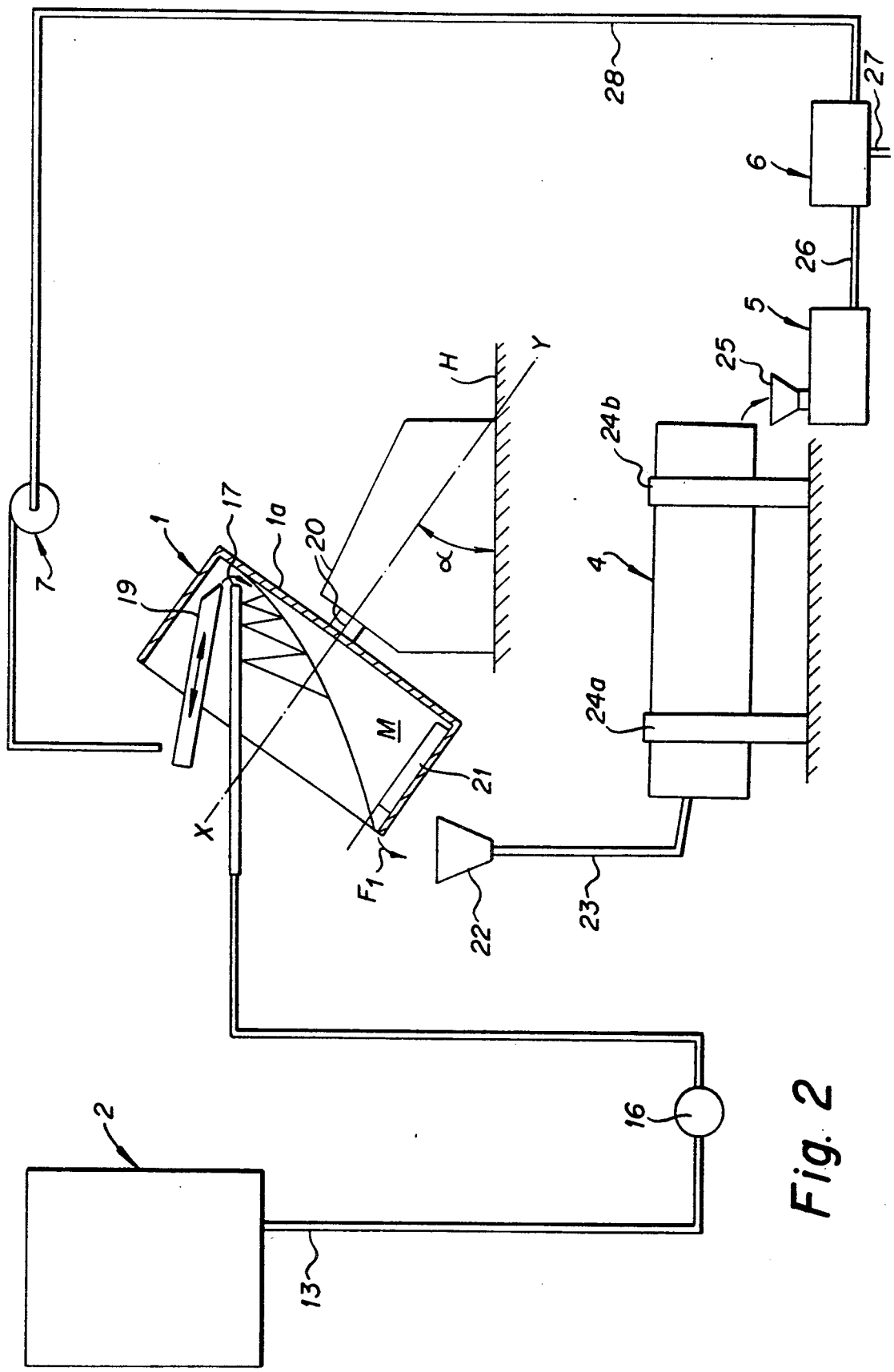
FIG. 2 is a dimensioned diametric section of a tablet prepared from compressible mannitol, this tablet serving to carry out certain measurements characterizing the compressibility of the mannitol obtained according to the invention as well as that of the compressible mannitols of the prior art.
Figure 2:
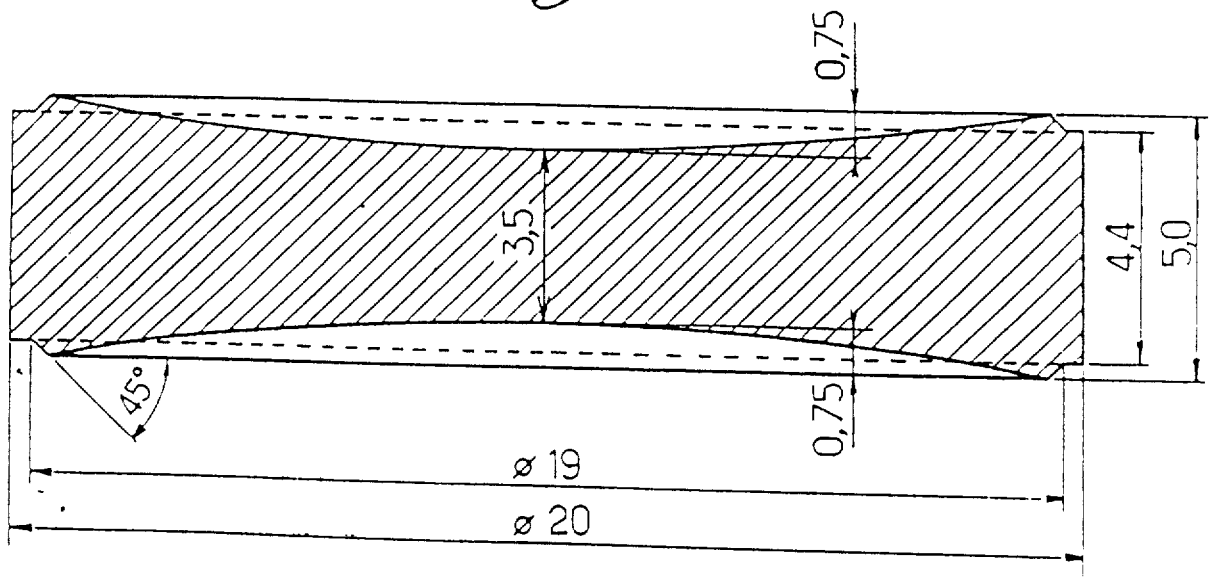

These tablets are round, biconcave and in the shape and with the dimensions resulting from FIG. 2.

Compressibility is expressed, as indicated above, by the value in Newtons of the breaking strength, measured on the tablets by means of an ERWEKA TB 24 hardness meter, equipped with a tablet support stand having a distance between supports of 10.55 mm (this apparatus is constructed by ERWEKA APPARATEBAU—6056 Heusenstamm—F.R.G.).

The results of these measurements as well as the granulometric distribution, the average granulometry, the content of lubricant constituted by magnesium stearate, the flow indices and the friability of various powders are collected in the table below.

TABLE

|  | Mannitol according to the invention (example) | Directly compressible mannitol commercial without binder | Directly compressible mannitol with binder (1.5% gelatin) |
|---|---|---|---|
| Granulometric) >1000 μm | 3 | 8.1 | 3 |
| distribution in %) >500 μm | 77 | 95 | 77 |
| cumulated by weight) >250 μm | 99 | 99 | 99 |
| Average granulometry (in μm) | 620 | 860 | 650 |
| Content in % of magnesium stearate | 0.5 | 0.8 | 1 |
| Breaking strength (in Newtons) | 114.7 | 59.8 | 130.4 |
| Friability (in %) | 75 | 81 | 70 |
| Flow (Carr index) | 85 | 82 | 85 |

It results from this table that the mannitol according to the invention has a friability intermediate between that of commercial mannitol (without binder) and that of mannitol (with binder) and that it shows a compressibility very close to that of mannitol with binder and very much greater than that of commercial mannitol without binder.

It exhibits in addition a free flow index sufficiently high—more precisely equal to that of mannitol including binder—to be employed commercially as a direct compression excipient.

Finally, all these values are reached for an average granulometry lower than that of the known binderless mannitol and even lower than that of mannitol with binder, which is important for the manufacture of pharmaceutical tablets weakly dosed with active principles.

The mannitol obtained by employing the method according to the invention will hence be advantageously used in replacement of directly compressible mannitols at present on the market, when they do not include the binder, have too low a compressibility and too great a friability.

As is self-evident and as results besides already from the foregoing, the invention is in no way limited to those of its types of application and embodiments which have been more especially envisaged; it encompasses, on the contrary, all modifications.

We claim:

1. Method of preparing directly compressible granular mannitol with improved compressibility and friability properties, the said compressibility being up to about 88% of that of mannitol with binder and up to about twice that of commercial mannitol without binder, the said friability being intermediate between that of commercial mannitol without binder and that of mannitol with binder, comprising selecting a raw material consisting essentially of powdered mannitol containing less than 4% by weight of water, subjecting said raw material to an extrusion treatment inside an extruder comprising a heating zone provided with a heating system, at least one screw and at least one extrusion die, selecting a flow rate for the raw material supplied the extruder, a diameter for the extrusion die and a rotary speed for the screw so that the said raw material travels through the heating zone within about two minutes, heating the heating zone to a temperature of 230° to 300° C. such that the temperature of the raw material is from 165° to 168° C. inside the extrusion die and before leaving it, whereby a proportion 30 to 90% of the said raw material is melted.

2. Directly compressible granular mannitol having improved compressibility and friability properties, the said compressibility being up to about 88% of that of mannitol with binder and up to about twice that of commercial manitol without binder, the said friability being intermediate between that of commercial mannitol without binder and that of mannitol with mannitol, the said mannitol being prepared by the process according to claim 1.

* * * * *

UNITED STATES PATENT AND TRADEMARK OFFICE
CERTIFICATE OF CORRECTION

PATENT NO. : 5,160,680

DATED : November 3, 1992

INVENTOR(S) : Serpelloni, et al.

It is certified that error appears in the above-identified patent and that said Letters Patent is hereby corrected as shown below:

In the Drawings:
Please replace Figure 2 with the attached Figure 2.

Please change claim 2, column 6, line 42 to read as follows:

--tol without binder and that of mannitol with binder,--

Signed and Sealed this

Twenty-first Day of December, 1993

Attest:

BRUCE LEHMAN

Attesting Officer          Commissioner of Patents and Trademarks